(12) United States Patent
Serban et al.

(10) Patent No.: US 12,562,260 B2
(45) Date of Patent: Feb. 24, 2026

(54) MULTI-MODAL FOUNDATIONAL MODELS FOR MEDICAL IMAGES USING MODALITY-SPECIFIC AND CROSS-MODALITY EXPERT SUBNETWORKS

(71) Applicant: Siemens Healthineers AG, Forchheim (DE)

(72) Inventors: Alexandru Constantin Serban, Constanta (RO); Florin-Cristian Ghesu, Baiersdorf (DE); Dominik Neumann, Erlangen (DE); Venkatesh Narasimha Murthy, Hillsborough, NJ (US); Bogdan Georgescu, Princeton, NJ (US)

(73) Assignee: Siemens Healthineers AG, Forchheim (DE)

( * ) Notice: Subject to any disclaimer, the term of this patent is extended or adjusted under 35 U.S.C. 154(b) by 265 days.

(21) Appl. No.: 18/494,790

(22) Filed: Oct. 26, 2023

(65) Prior Publication Data

US 2025/0140382 A1 May 1, 2025

(51) Int. Cl.
*G06K 9/00* (2022.01)
*G06V 10/774* (2022.01)
(Continued)

(52) U.S. Cl.
CPC ........... *G16H 30/40* (2018.01); *G06V 10/774* (2022.01); *G06V 10/95* (2022.01); *G06V 20/50* (2022.01);
(Continued)

(58) Field of Classification Search
CPC ...... G16H 30/40; G06V 10/774; G06V 10/95; G06V 20/50; G06V 10/82; G06V 2201/031; G06V 2201/03
See application file for complete search history.

(56) References Cited

U.S. PATENT DOCUMENTS

2019/0114773 A1* 4/2019 Song ..................... G06F 18/253

OTHER PUBLICATIONS

Extended European Search Report (EESR) mailed Mar. 5, 2025 in corresponding European Patent Application No. 24208292.3.
(Continued)

*Primary Examiner* — Xin Jia

(57) ABSTRACT

Systems and methods for performing a medical imaging analysis task using a machine learning based model (e.g., a foundational model) are provided. One or more input medical images are received. One or more modality-specific expert subnetworks of the machine learning based model are selected for performing a first processing of the one or more input medical images. The first processing of the one or more input medical images is performed for performing a medical imaging analysis task using the one or more selected modality-specific expert subnetworks. Results of the first processing are merged into one or more sets of merged results. One or more cross-modality expert subnetworks of the machine learning based model are selected for performing a second processing of the one or more sets of merged results. The second processing of the one or more sets of merged results is performed for performing the medical imaging analysis task using the one or more selected cross-modality expert subnetworks. Results of the second processing are output.

20 Claims, 6 Drawing Sheets

100

Receive one or more input medical images
102

Select one or more modality-specific expert subnetworks of a machine learning based model for performing a first processing of the one or more input medical images
104

Perform the first processing of the one or more input medical images for performing a medical imaging analysis task using the one or more selected modality-specific expert subnetworks
106

Merge results of the first processing into one or more sets of merged results
108

Select one or more cross-modality expert subnetworks of the machine learning based model for performing a second processing of the one or more sets of merged results
110

Perform the second processing of the one or more sets of merged results for performing the medical imaging analysis task using the one or more selected cross-modality expert subnetworks
112

Output results of the second processing
114

(51) Int. Cl.
    *G06V 10/94*        (2022.01)
    *G06V 20/50*        (2022.01)
    *G16H 30/40*        (2018.01)
    *G06V 10/82*        (2022.01)

(52) U.S. Cl.
    CPC ........ *G06V 10/82* (2022.01); *G06V 2201/031*
                                                (2022.01)

(56)                References Cited

OTHER PUBLICATIONS

Guo Zhe et al: "Deep Learning-Based Image 1-15 INV. Segmentation on Multimodal Medical Imaging", IEEE Transactions on Radiation and Plasma Medical Sciences, IEEE, vol. 3, No. 2, Mar. 1, 2019; pp. 162-169.

Radford et al., "Learning transferable visual models from natural language supervision", arXiv:2103.00020v1, 2021, pp. 1-48.

Driess et al., "PaLM-E: An embodied multimodal language model", arXiv:2303.03378v1, 2023, 18 pgs.

Ghesu et al., "Contrastive self-supervised learning from 100 million medical images", arXiv:2201.01283v1, 2022, pp. 1-13.

Riquelme et al., "Scaling vision with sparse mixture of experts", Advances in Neural Information Processing Systems, 2021, pp. 1-13.

Du et al., "GlaM: Efficient scaling of language models with mixture-of-experts", Proceedings of the 39th International Conference on Machine Learning, 2022, 23 pgs.

Baevsky et al., "Efficient self-supervised learning with contextualized target representations for vision, speech and language", Proceedings of the 40th International Conference on Machine Learning, 2023, pp. 1-14.

* cited by examiner

Figure 1:
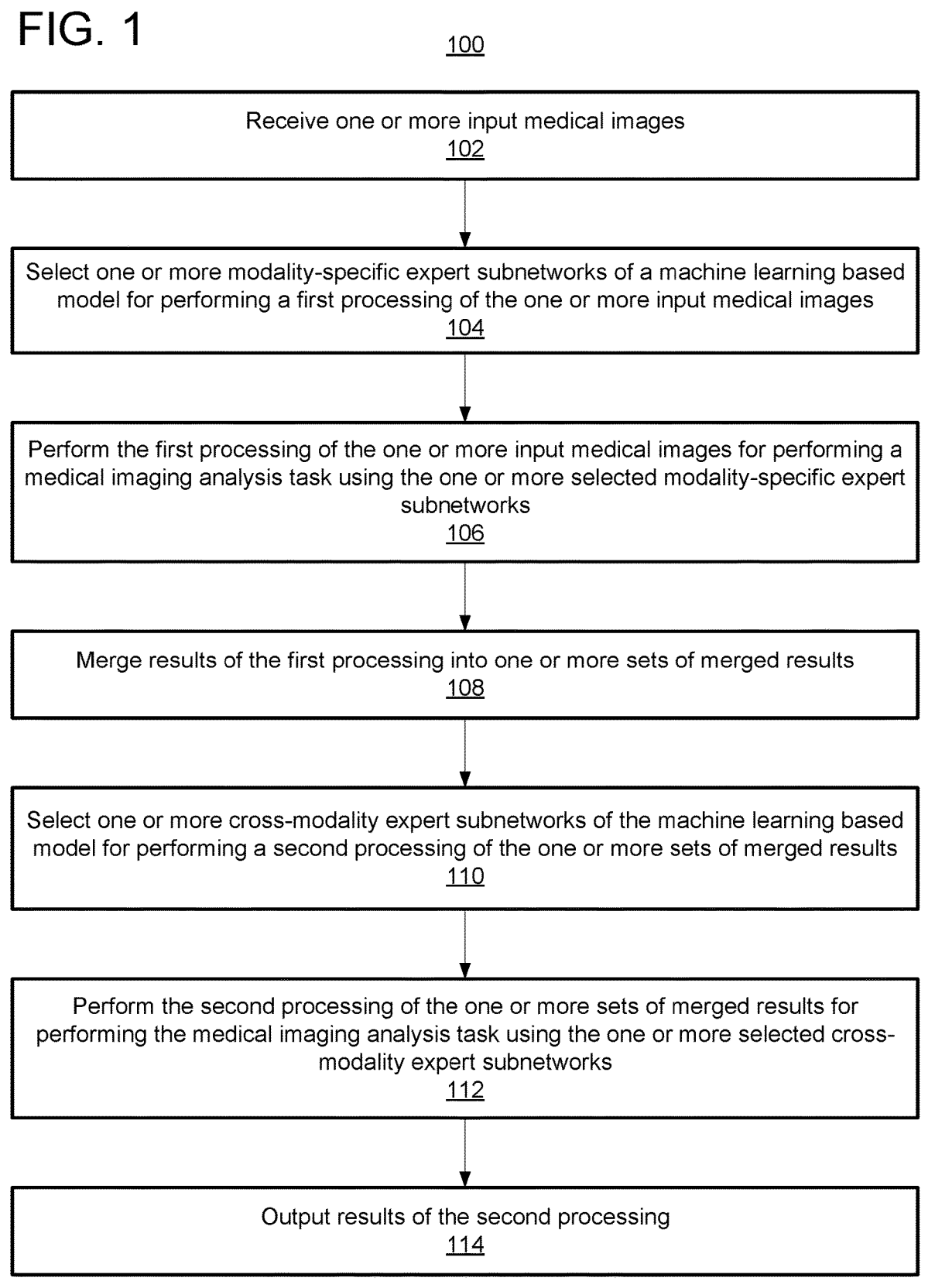

Receive one or more input medical images
<u>102</u>

Select one or more modality-specific expert subnetworks of a machine learning based model for performing a first processing of the one or more input medical images
<u>104</u>

Perform the first processing of the one or more input medical images for performing a medical imaging analysis task using the one or more selected modality-specific expert subnetworks
<u>106</u>

Merge results of the first processing into one or more sets of merged results
<u>108</u>

Select one or more cross-modality expert subnetworks of the machine learning based model for performing a second processing of the one or more sets of merged results
<u>110</u>

Perform the second processing of the one or more sets of merged results for performing the medical imaging analysis task using the one or more selected cross-modality expert subnetworks
<u>112</u>

Output results of the second processing
<u>114</u>

200

300

312-A → Cross-modality expert 1          Cross-modality expert 2 ← 312-B

310 → Cross-modality expert selection

308 → Merge Module

306-A → CT Expert 1          CT expert 2 ← 306-B

304 → In-modality expert selection

302 → CT Data

500

MULTI-MODAL FOUNDATIONAL MODELS FOR MEDICAL IMAGES USING MODALITY-SPECIFIC AND CROSS-MODALITY EXPERT SUBNETWORKS

TECHNICAL FIELD

The present invention relates generally to large-scale machine learning based foundational models, and in particular to multi-modal foundational models for medical images using modality-specific and cross-modality expert subnetworks.

BACKGROUND

Foundational models are large-scale machine learning models that can be adapted for performing many different applications. Foundational models are trained on a broad data set and fine-tuned for a variety of tasks. Conventionally, the training of multi-modal foundational models typically requires pairs of training data from different modalities, such as, e.g., text and images, text and speech, speech and images, etc. However, the medical domain presents unique and novel challenges for training foundational models due to data heterogeneity, particularly with medical images of different modalities acquired using different types of scanners. Collecting large scale pairs of medical images of different modalities is not feasible, as the costs associated with imaging the same patients with multiple scanners is prohibitively high, particularly absent any clinical reason to do so.

Recently, auxiliary tasks that do not require labels have been proposed for training foundational models for medical images of different modalities via self-supervised learning. However, without pairs of medical images, all images must be processed by the same encoder, leading to entangled representations across modalities and reducing the representation power of the foundational models. Contrastive learning methods often used for self-supervised learning are also not sufficient, as they require negative anchors both in- and cross-modality. Such contrastive learning methods may result in representations that are significantly distinct for in-modality, but less distinct for cross-modality.

BRIEF SUMMARY OF THE INVENTION

In accordance with one or more embodiments, systems, methods, and computer readable mediums storing computer program instructions for performing a medical imaging analysis task using a machine learning based model (e.g., a foundational model) are provided. One or more input medical images are received. One or more modality-specific expert subnetworks of the machine learning based model are automatically selected for performing a first processing of the one or more input medical images. The first processing of the one or more input medical images is performed for performing a medical imaging analysis task using the one or more selected modality-specific expert subnetworks. Results of the first processing are merged into one or more sets of merged results. One or more cross-modality expert subnetworks of the machine learning based model are selected for performing a second processing of the one or more sets of merged results. The second processing of the one or more sets of merged results is performed for performing the medical imaging analysis task using the one or more selected cross-modality expert subnetworks. Results of the second processing are output.

In one embodiment, the machine learning based model is trained via self-supervised learning.

In one embodiment, the first processing of the one or more input medical images is performed by processing modality-specific data of the one or more input medical images using the one or more selected modality-specific expert subnetworks.

In one embodiment, the second processing of the one or more sets of merged results is performed by integrating the one or more sets of merged results between each other.

In one embodiment, a number of modality-specific expert subnetworks in the machine learning based network is learned for each modality during training of the machine learning based network. In another embodiment, a number of modality-specific expert subnetworks in the machine learning based network is predefined for each modality.

In one embodiment, a number of cross-modality expert subnetworks in the machine learning based network is learned during training of the machine learning based network.

In one embodiment, a number of layers and a number of parameters of each of the layer for each modality-specific expert subnetwork and each cross-modality expert subnetworks in the machine learning based network are defined based on resource availability.

In one embodiment, the machine learning based model is a foundational model.

These and other advantages of the invention will be apparent to those of ordinary skill in the art by reference to the following detailed description and the accompanying drawings.

BRIEF DESCRIPTION OF THE DRAWINGS

FIG. 1 shows a method for performing a medical imaging analysis task using a machine learning based model comprising modality-specific expert subnetworks and cross-modality expert subnetworks, in accordance with one or more embodiments;

DETAILED DESCRIPTION

The present invention generally relates to methods and systems for multi-modal foundational models for medical images using modality-specific and cross-modality expert subnetworks. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system. Further, reference herein to pixels of an image may refer equally to voxels of an image and vice versa.

Embodiments described herein provide for foundational models trained using in- and cross-modality mixture-of-experts. Such foundational models comprise modality-specific expert subnetworks preserving modality-specific properties and cross-modality expert subnetworks integrating cross-modality features, along with an in-modality expert selection module for selecting the appropriate modality-specific expert subnetworks and a cross-modality expert selection module for selecting the appropriate cross-modality expert subnetworks. Advantageously, foundational models in accordance with embodiments described herein 1) promote disentangled representations during training, 2) ensure scalability in the number of parameters, 3) ensure fast run time for modality specific inference, and 4) enable cross-modality information exchange.

Figure 2:
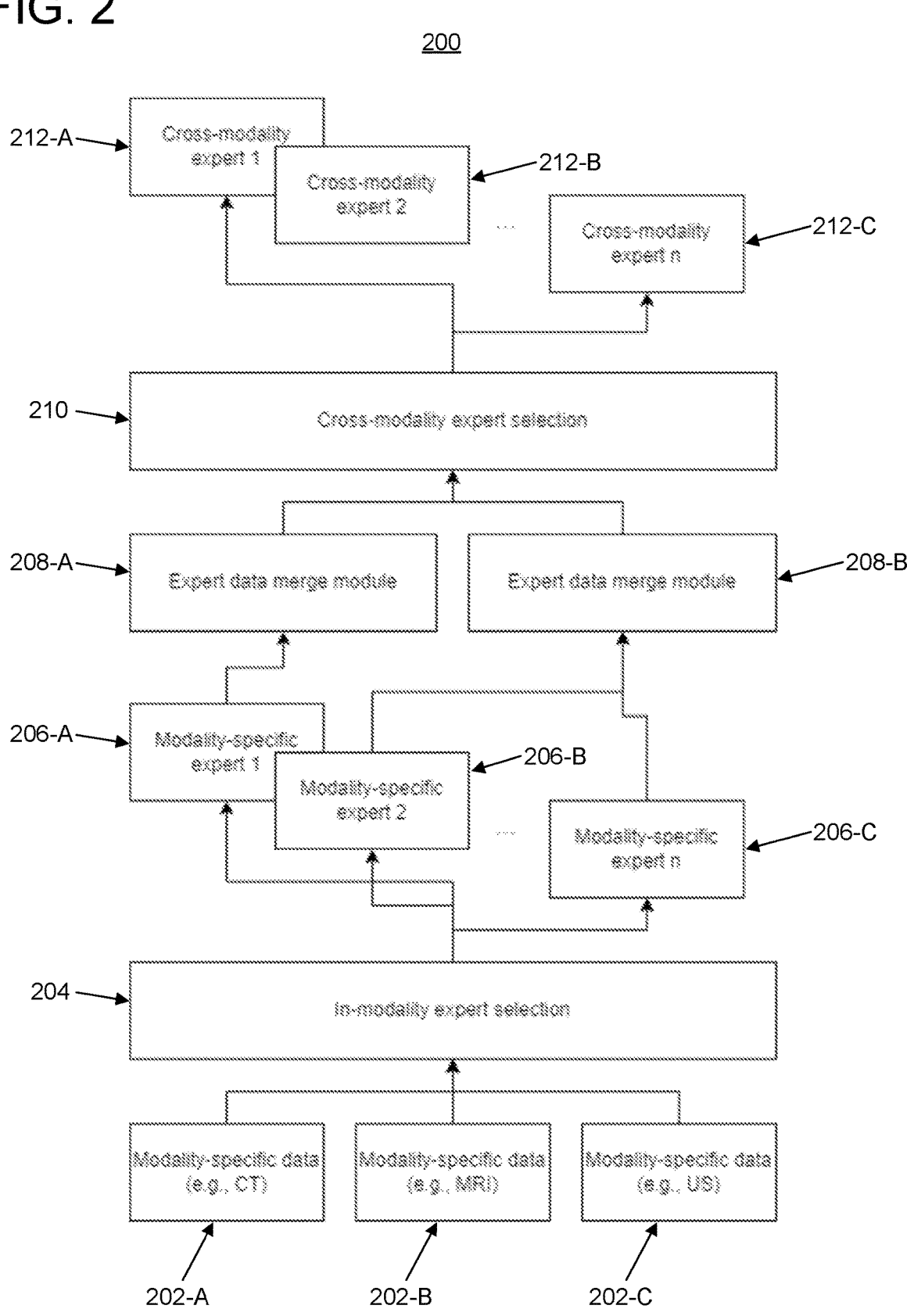
FIG. 2 shows a workflow for performing a medical imaging analysis task using a machine learning based model comprising modality-specific expert subnetworks and cross-modality expert subnetworks, in accordance with one or more embodiments.

FIG. 1 shows a method 100 for performing a medical imaging analysis task using a machine learning based model comprising modality-specific expert subnetworks and cross-modality expert subnetworks, in accordance with one or more embodiments. The steps of method 100 may be performed by one or more suitable computing devices, such as, e.g., computer 602 of FIG. 6. FIG. 2 shows a workflow 200 for performing a medical imaging analysis task using a machine learning based model comprising modality-specific expert subnetworks and cross-modality expert subnetworks, in accordance with one or more embodiments. FIG. 1 and FIG. 2 will be described together. Method 100 of FIG. 1 and workflow 200 of FIG. 2 are performed during an online or inference stage for performing the medical imaging analysis task using the machine learning based model that was trained during a prior offline or training stage.

At step 102 of FIG. 1, one or more input medical images are received. The one or more input medical images may depict an anatomical object(s) of interest of a patient, such as, e.g., organs, bones, vessels, lesions, etc. The one or more input medical images may be of any suitable modality or modalities, such as, e.g., CT (computed tomograph), MRI (magnetic resonance imaging), US (ultrasound), X-ray, or any other medical imaging modality or combinations of medical imaging modalities. The one or more input medical images may be 2D (two dimensional) images and/or 3D (three dimensional) volumes. The one or more input medical images may be received directly from an image acquisition device (e.g., image acquisition device 614 of FIG. 6) as the medical images are acquired, may be received by loading previously acquired medical images from a storage or memory of a computer system (e.g., computer 602 of FIG. 6), or may be received from a remote computer system (e.g., computer 602 of FIG. 6).

In one example, as shown in workflow 200 of FIG. 2, the one or more input medical images may be modality-specific data 202-A, 202-B, and 202-C (collectively referred to as modality-specific data 202) respectively corresponding to CT medical images, MRI medical images, and US medical images.

At step 104 of FIG. 1, one or more modality-specific expert subnetworks of a machine learning based model are selected for performing a first processing of the one or more input medical images. An in-modality expert selection module of the machine learning based model receives the one or more input medical images, automatically selects the one or more modality-specific expert subnetworks, and routes the one or more input medical images to the one or more selected modality-specific expert subnetworks for performing the first processing. In one example, as shown in workflow 200 of FIG. 2, modality-specific expert subnetworks 206-A, 206-B, and 206-C (collectively referred to as modality-specific expert subnetworks 206) of a foundational model are selected by in-modality expert selection module 204 of the foundational model for performing a first processing of modality-specific data 202.

In one embodiment, the machine learning based model is a foundational model. However, the machine learning based model may be implemented according to any suitable machine learning based architecture (e.g., neural network architectures). The one or more modality-specific expert subnetworks are branches of the machine learning based model trained to process modality-specific data of the one or more input medical images for specific modalities. The one or more modality-specific expert subnetworks may be implemented using any suitable machine learning based architecture, such as, e.g., convolutional neural network layers or transformer neural network layers. The architecture of the one or more modality-specific expert subnetworks may be the same or different.

In one embodiment, the one or more modality-specific expert subnetworks are learned during a prior training of the machine learning based model and are not predefined (e.g., by a user). For example, during the training of the machine learning based model, a number of modality-specific expert subnetworks to include in the machine learning based model and specialized tasks performed by each of the modality-specific expert subnetworks are learned. Such specialized tasks may include, for example, tasks specializing in different modalities, specializing in different anatomical objects, specializing in different imaging resolutions, specializing in determining edges, organs, anatomical information, etc. based on the modality, robust to contrast changes specific to a modality, robust to modality-specific artefacts (e.g., due to the image acquisition technique), etc. The information learned from performing the specialized tasks may be shared cross-modality by the modality-specific expert subnetworks. In other embodiments, the number of modality-specific expert subnetworks may be predefined for each modality by a user and specialized tasks performed by each of the modality-specific expert subjects are learned during the training of the machine learning based model. In any of the embodiments, the number of modality-specific expert subnetworks may differ per modality, as some modalities can be more difficult to represent.

The architecture of the modality-specific expert subnetworks is predefined. For example, in one embodiment, a number of layers and a number of parameters in each layer (i.e., a depth and a width) of each of the modality-specific expert subnetworks may be predefined (e.g., by a user) based on resource availability. In another embodiment, a number of layers and a number of parameters in each layer of each of the modality-specific expert subnetworks may be automatically determined, e.g., using any suitable well-known approach. The number of layers of the modality-specific expert subnetworks may be a single layer or a plurality of layers.

At step 106 of FIG. 1, the first processing of the one or more input medical images is performed for performing a medical imaging analysis task using the one or more selected modality-specific expert subnetworks. In one example, as shown in workflow 200 of FIG. 2, the first processing is performed using modality-specific expert subnetworks 206. Each of the one or more selected modality-specific expert subnetworks perform different specialized tasks contributing to the performance of the first processing. Each of the one or more selected modality-specific expert subnetworks receive as input at least one of the one or more input medical images and generates as output results contributing to the first processing.

At step 108 of FIG. 1, results of the first processing are merged into one or more sets of merged results. The results of the first processing are merged by one or more expert data merge modules. The expert data merge modules are branches of the machine learning based model that learn to merge results of the first processing as appropriate during the training of the machine learning based model. In one example, as shown in workflow 200 of FIG. 2, results of the first processing output by modality-specific expert subnetworks 206 are merged into one or more sets of merged results by expert data merge module 208-A and 208-B (collectively referred to as expert data merge module 208). In particular, results of the first processing output by modality-specific expert subnetwork 206-A are merged by expert data merge module 208-A into a first set of merged results and results of the first processing output by modality-specific expert subnetworks 206-B and 206-C are merged by expert data merge module 208-B into a second set of merged results.

At step 110 of FIG. 1, one or more cross-modality expert subnetworks of the machine learning based model are selected for performing a second processing of the one or more sets of merged results. A cross-modality expert selection module of the machine learning based model receives as input the one or more sets of merged results, selects the one or more cross-modality expert subnetworks, and routes the one or more sets of merged results to the one or more selected cross-modality expert subnetworks for performing the second processing. In one example, as shown in workflow 200 of FIG. 2, cross-modality expert subnetworks 212-A, 212-B, and 212-C (collectively referred to as cross-modality expert subnetworks 212) of the foundational model are selected by cross-modality expert selection module 210 of the foundational model for performing a second processing of the one or more sets of merged results output from expert data merge module 208.

The one or more cross-modality expert subnetworks are branches of the machine learning based model trained to integrate the merged results of the one or more modality-specific expert subnetworks cross-modality (i.e., between each other). The cross-modality expert subnetworks enable similar representations for similar concepts across different modalities. For example, similar organs (or other anatomical objects of interest) depicted in medical images of different modalities will result in similar representations. The one or more cross-modality expert subnetworks may be implemented using any suitable machine learning based architecture, such as, e.g., convolutional neural network layers or transformer neural network layers. The architecture of the one or more cross-modality expert subnetworks may be the same or different.

In one embodiment, the one or more cross-modality expert subnetworks are learned during the training of the machine learning based model. For example, during the training of the machine learning based model, a number of cross-modality expert subnetworks to include in the machine learning based model and specialized tasks performed by each of the cross-modality expert subnetworks (e.g., specializing in integration of features between particular modalities, different anatomical objects, different image resolutions, etc.) are learned. Such specialized tasks may include, for example, tasks specializing in integration of features between particular modalities, specializing in different anatomical objects, specializing in different image resolutions, specializing in the identification of organs given different properties of the modality, specializing in relationships between anatomical structures (e.g., the stomach is close to the liver), specializing in the detection of margins, etc.

The architecture of the cross-modality expert subnetworks is predefined. For example, a number of layers and a number of parameters in each layer (i.e., a depth and a width) of each of the cross-modality expert subnetworks may be predefined by a user based on resource availability. The number of layers of the cross-modality expert subnetworks may be a single layer or a plurality of layers.

At step 112 of FIG. 1, the second processing of the one or more sets of merged results is performed for performing the medical imaging analysis task using the one or more selected cross-modality expert subnetworks. In one example, as shown in workflow 200 of FIG. 2, the second processing is performed using cross-modality expert subnetworks 212. Each of the one or more selected cross-modality expert subnetworks perform different tasks contributing to the performance of the second processing. Each of the one or more selected cross-modality expert subnetworks receives as input at least one of the one or more sets of merged results and generates as output results contributing to the second processing. The results output by the one or more selected cross-modality expert subnetworks represent results of the medical imaging analysis task. The medical imaging analysis task may comprise any suitable medical imaging analysis task, such as, e.g., detection, classification, segmentation, etc.

At step 114 of FIG. 1, results of the second processing are output. In one embodiment, the results of the second processing may be output to another layer of expert subnetworks (e.g., in-modality expert subnetworks or cross-modality expert subnetworks). In another embodiment, e.g., where the one or more selected cross-modality expert subnetworks is a final layer of the machine learning based model, the results of the second processing may be output as the final results of the medical imaging analysis task. The results of the second processing can be output by, for example, displaying the results of the assessment on a display device of a computer system, storing the results of the second processing on a memory or storage of a computer system, or by transmitting the results of the second processing to a remote computer system.

The machine learning based model is trained during a prior offline or training stage to perform a medical imaging analysis task based on a set of training images of a plurality of different modalities. The machine learning based model may be trained via self-supervised learning, e.g., using contextualized target prediction. Once trained, the machine learning based model may be applied during an online or inference to perform the medical imaging analysis task, for example, to perform method 100 of FIG. 1 or workflow 200 of FIG. 2.

In one embodiment, method 100 of FIG. 1 and workflow 200 of FIG. 2 may be performed on the one or more input medical images for a single modality to efficiently perform a medical imaging analysis task. When the one or more input medical images are of only a single modality, the in- and cross-modality expert selection modules will select and run only specific modality-specific expert subnetworks and cross-modality expert subnetworks for that modality. Depending on the complexity of the modality, both the in- and cross-modality expert selection modules can potentially select more or less specific modality-specific expert subnetworks and cross-modality expert subnetworks. Since only some expert subnetworks will process the data, the foundational model gains efficiency while retaining scale. A workflow for efficiently performing a medical imaging analysis task on input medical images of a single modality is shown in FIG. 3.

Figure 3:
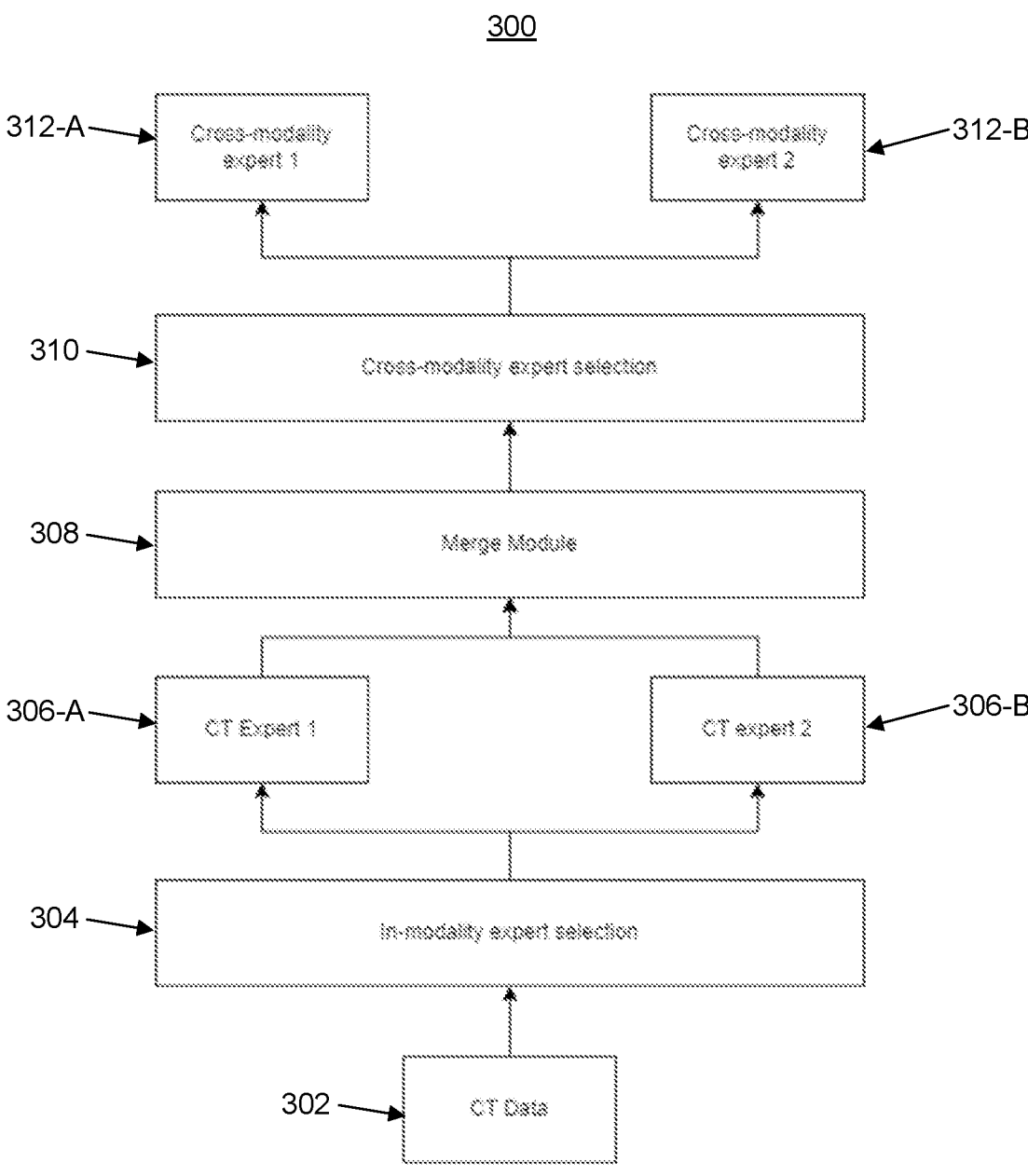
FIG. 3 shows a workflow for efficiently performing a medical imaging analysis task on input medical images of a single modality using a machine learning based model comprising modality-specific expert subnetworks and cross-modality expert subnetworks, in accordance with one or more embodiments.

FIG. 3 shows a workflow 300 for efficiently performing a medical imaging analysis task on input medical images of a single modality using a machine learning based model comprising modality-specific expert subnetworks and cross-modality expert subnetworks, in accordance with one or more embodiments. In workflow 300, CT data 302 (e.g., images) is received by in-modality expert selection module 304 for a machine learning based model. In-modality expert selection module 304 selects CT modality-specific expert subnetworks 306-A and 306-B (collectively referred to as CT modality-specific expert subnetworks 306) and CT modality-specific expert subnetworks 306 perform a first processing of CT data 302 for performing a medical imaging analysis task. Merge module 308 merges results of the first processing output by CT modality-specific expert subnetworks 306 into one or more sets of merged results. Cross-modality expert selection module 310 selects cross-modality expert subnetworks 312-A and 312-B (collectively referred to as cross-modality expert subnetworks 312) and cross-modality expert subnetworks 312 perform a second processing of the one or more sets of merged results for performing a medical imaging analysis task.

Advantageously, the machine learning based model (e.g., foundational model) in accordance with embodiments described herein provide for a composition of different expert subnetworks, which ensures modularity. In one embodiment, the trained machine learning based model may be finetuned for processing medical images of a new modality. To extend the trained machine learning based model, new modality-specific and cross-modality expert subnetworks are added to the machine learning based model and finetuned. To ensure continual learning and avoid catastrophic forgetting, when the newly added expert subnetworks are trained, the already trained expert subnetworks can be finetuned at a slower pace than the newly added expert subnetworks. The flexibility gained enabled by the machine learning based model may significantly reduce maintenance costs while enabling continual learning.

While embodiment described herein are described with respect to input medical images of different medical imaging modalities, embodiments described herein are not so limited. In one embodiment, the one or more input medical images may instead be any type or types of data (e.g., text, speech, images, etc.). For example, the one or more input medical images may be text-based data and the language of the text may be considered the modality. The modality-specific expert subnetworks may specialize in particular languages and the cross-modality expert subnetworks may integrate common language representations. In another example, the one or more input medical images may be multi-modal data comprising speech in different languages; text and speech; text, speech, and vision; or any other mix of modalities relevant for performing the task.

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, certain embodiments described herein are described with respect to methods and systems utilizing trained machine learning based models, as well as with respect to methods and systems for training machine learning based models. Features, advantages or alternative embodiments herein can be assigned to the other claimed objects and vice versa. In other words, claims for methods and systems for training a machine learning based model can be improved with features described or claimed in context of the methods and systems for utilizing a trained machine learning based model, and vice versa.

In particular, the trained machine learning based models applied in embodiments described herein can be adapted by the methods and systems for training the machine learning based models. Furthermore, the input data of the trained machine learning based model can comprise advantageous features and embodiments of the training input data, and vice versa. Furthermore, the output data of the trained machine learning based model can comprise advantageous features and embodiments of the output training data, and vice versa.

In general, a trained machine learning based model mimics cognitive functions that humans associate with other human minds. In particular, by training based on training data, the trained machine learning based model is able to adapt to new circumstances and to detect and extrapolate patterns.

In general, parameters of a machine learning based model can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based model can be adapted iteratively by several steps of training.

In particular, a trained machine learning based model can comprise a neural network and/or a Bayesian network, and/or the trained machine learning based model can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 4:
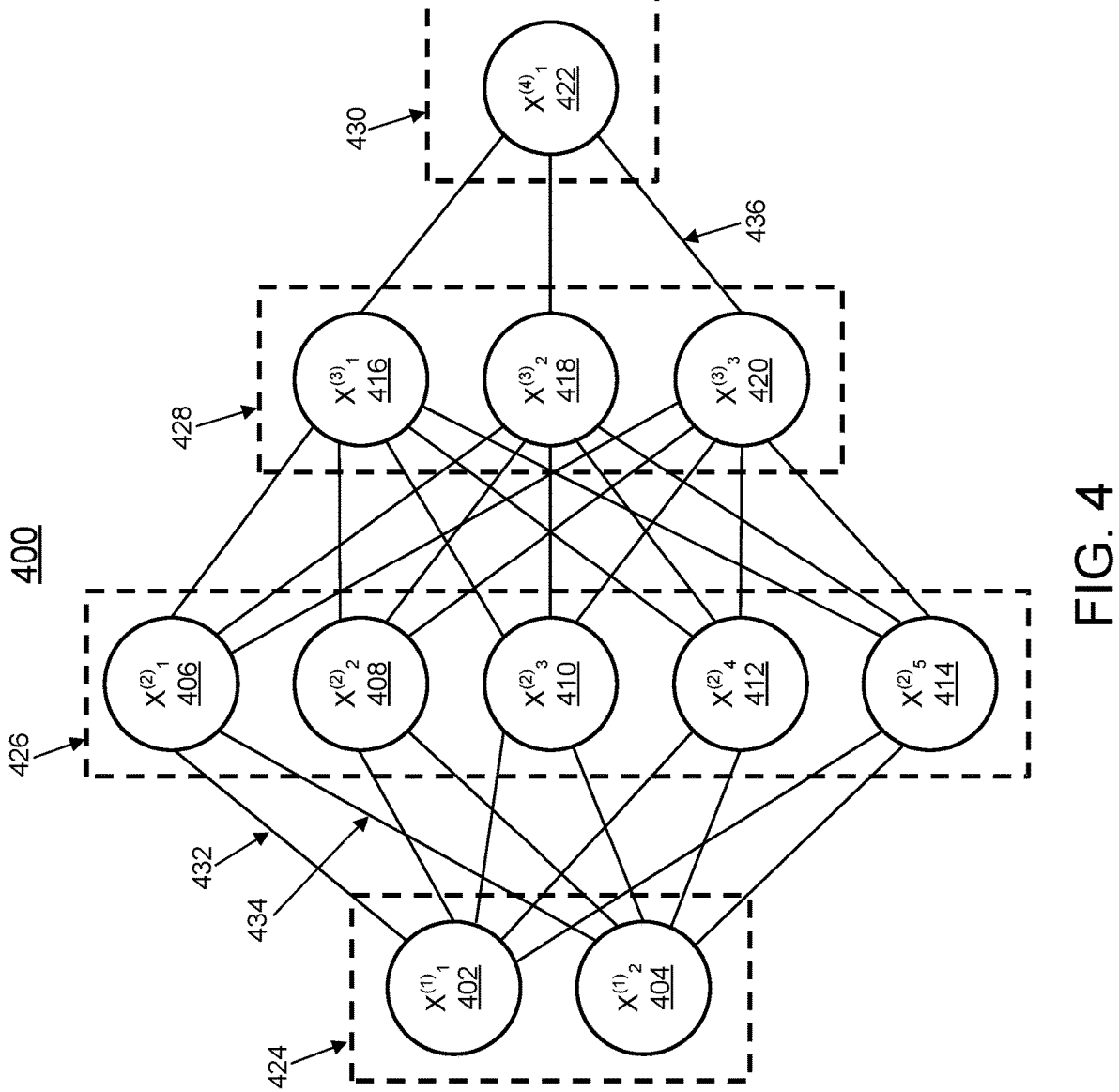
FIG. 4 shows an exemplary artificial neural network that may be used to implement one or more embodiments.

FIG. 4 shows an embodiment of an artificial neural network 400, in accordance with one or more embodiments. Alternative terms for "artificial neural network" are "neural network", "artificial neural net" or "neural net". Machine learning networks described herein, such as, e.g., the machine learning based model utilized in method 100 of FIG. 1, the machine learning based model comprising in-modality expert selection module 204, modality-specific expert subnetworks 206, expert data merge module 208, cross-modality expert selection module 210, and cross-modality expert subnetwork 212 in workflow 200 of FIG. 2, and the machine learning based model comprising in-modality expert selection module 304, CT modality-specific expert subnetworks 306, merge module 308, cross-modality expert selection module 310, and cross-modality expert subnetwork 312 in workflow 300 of FIG. 3, may be implemented using artificial neural network 400.

The artificial neural network 400 comprises nodes 402-422 and edges 432, 434, . . . , 436, wherein each edge 432, 434, . . . , 436 is a directed connection from a first node 402-422 to a second node 402-422. In general, the first node 402-422 and the second node 402-422 are different nodes 402-422, it is also possible that the first node 402-422 and the second node 402-422 are identical. For example, in FIG. 4, the edge 432 is a directed connection from the node 402 to the node 406, and the edge 434 is a directed connection from the node 404 to the node 406. An edge 432, 434, . . . , 436 from a first node 402-422 to a second node 402-422 is also denoted as "ingoing edge" for the second node 402-422 and as "outgoing edge" for the first node 402-422.

In this embodiment, the nodes 402-422 of the artificial neural network 400 can be arranged in layers 424-430, wherein the layers can comprise an intrinsic order introduced by the edges 432, 434, . . . , 436 between the nodes 402-422. In particular, edges 432, 434, . . . , 436 can exist only between neighboring layers of nodes. In the embodiment shown in FIG. 4, there is an input layer 424 comprising only nodes 402 and 404 without an incoming edge, an output layer 430 comprising only node 422 without outgoing edges, and hidden layers 426, 428 in-between the input layer 424 and the output layer 430. In general, the number of hidden layers 426, 428 can be chosen arbitrarily. The number of nodes 402 and 404 within the input layer 424 usually relates to the number of input values of the neural network 400, and the number of nodes 422 within the output layer 430 usually relates to the number of output values of the neural network 400.

In particular, a (real) number can be assigned as a value to every node 402-422 of the neural network 400. Here, $x^{(n)}_i$ denotes the value of the i-th node 402-422 of the n-th layer 424-430. The values of the nodes 402-422 of the input layer 424 are equivalent to the input values of the neural network 400, the value of the node 422 of the output layer 430 is equivalent to the output value of the neural network 400. Furthermore, each edge 432, 434, . . . , 436 can comprise a weight being a real number, in particular, the weight is a real number within the interval [−1, 1] or within the interval [0, 1]. Here, $w^{(m,n)}_{i,j}$ denotes the weight of the edge between the i-th node 402-422 of the m-th layer 424-430 and the j-th node 402-422 of the n-th layer 424-430. Furthermore, the abbreviation $w^{(n)}_{i,j}$ is defined for the weight $w^{(n,n+1)}_{i,j}$.

In particular, to calculate the output values of the neural network 400, the input values are propagated through the neural network. In particular, the values of the nodes 402-422 of the (n+1)-th layer 424-430 can be calculated based on the values of the nodes 402-422 of the n-th layer 424-430 by $$x^{(n+1)}_j = f\left(\sum_i x^{(n)}_i \cdot w^{(n)}_{i,j}\right).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 424 are given by the input of the neural network 400, wherein values of the first hidden layer 426 can be calculated based on the values of the input layer 424 of the neural network, wherein values of the second hidden layer 428 can be calculated based in the values of the first hidden layer 426, etc.

In order to set the values $w^{(m,n)}_{i,j}$ for the edges, the neural network 400 has to be trained using training data. In particular, training data comprises training input data and training output data (denoted as $t_i$). For a training step, the neural network 400 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 400 (backpropagation algorithm). In particular, the weights are changed according to $$w'^{(n)}_{i,j} = w^{(n)}_{i,j} - \gamma \cdot \delta^{(n)}_j \cdot x^{(n)}_i$$

wherein $\gamma$ is a learning rate, and the numbers $\delta^{(n)}_j$ can be recursively calculated as $$\delta^{(n)}_j = \left(\sum_k \delta^{(n+1)}_k \cdot w^{(n+1)}_{j,k}\right) \cdot f'\left(\sum_i x^{(n)}_i \cdot w^{(n)}_{i,j}\right)$$

based on $\delta^{(n+1)}_j$, if the (n+1)-th layer is not the output layer, and $$\delta^{(n)}_j = \left(x^{(n+1)}_k - t^{(n+1)}_j\right) \cdot f'\left(\sum_i x^{(n)}_i \cdot w^{(n)}_{i,j}\right)$$

if the (n+1)-th layer is the output layer 430, wherein f' is the first derivative of the activation function, and $y^{(n+1)}_j$ is the comparison training value for the j-th node of the output layer 430.

Figure 5:
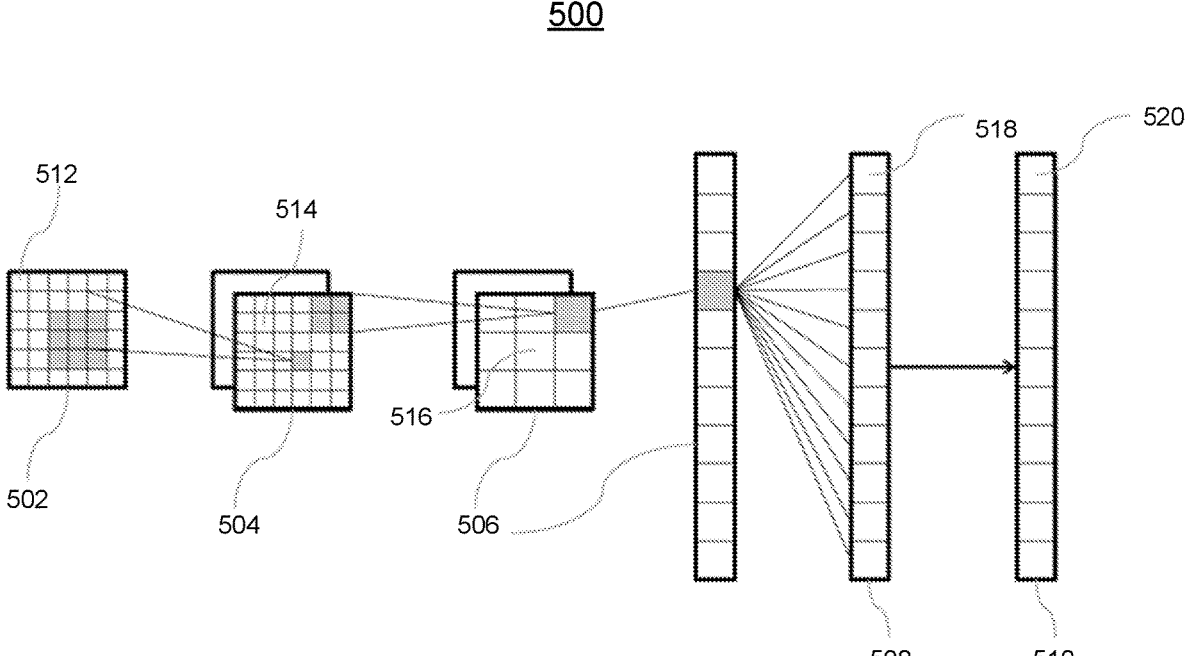
FIG. 5 shows a convolutional neural network that may be used to implement one or more embodiments.

FIG. 5 shows a convolutional neural network 500, in accordance with one or more embodiments. Machine learning networks described herein, such as, e.g., the machine learning based model utilized in method 100 of FIG. 1, the machine learning based model comprising in-modality expert selection module 204, modality-specific expert subnetworks 206, expert data merge module 208, cross-modality expert selection module 210, and cross-modality expert subnetwork 212 in workflow 200 of FIG. 2, and the machine learning based model comprising in-modality expert selection module 304, CT modality-specific expert subnetworks 306, merge module 308, cross-modality expert selection module 310, and cross-modality expert subnetwork 312 in workflow 300 of FIG. 3, may be implemented using convolutional neural network 500.

In the embodiment shown in FIG. 5, the convolutional neural network comprises 500 an input layer 502, a convolutional layer 504, a pooling layer 506, a fully connected layer 508, and an output layer 510. Alternatively, the convolutional neural network 500 can comprise several convolutional layers 504, several pooling layers 506, and several fully connected layers 508, as well as other types of layers. The order of the layers can be chosen arbitrarily, usually fully connected layers 508 are used as the last layers before the output layer 510.

In particular, within a convolutional neural network 500, the nodes 512-520 of one layer 502-510 can be considered to be arranged as a d-dimensional matrix or as a d-dimensional image. In particular, in the two-dimensional case the value of the node 512-520 indexed with i and j in the n-th layer 502-510 can be denoted as $x^{(n)}_{[i,j]}$. However, the arrangement of the nodes 512-520 of one layer 502-510 does not have an effect on the calculations executed within the convolutional neural network 500 as such, since these are given solely by the structure and the weights of the edges.

In particular, a convolutional layer 504 is characterized by the structure and the weights of the incoming edges forming a convolution operation based on a certain number of kernels. In particular, the structure and the weights of the incoming edges are chosen such that the values $x^{(n)}_k$ of the nodes 514 of the convolutional layer 504 are calculated as a convolution $x^{(n)}_k = K_k * x^{(n-1)}$ based on the values $x^{(n-1)}$ of the nodes 512 of the preceding layer 502, where the convolution * is defined in the two-dimensional case as $$x^{(n)}_k[i, j] = \left(K_k * x^{(n-1)}\right)[i, j] = \sum_{i'}\sum_{j'} K_k[i', j'] \cdot x^{(n-1)}[i - i', j - j'].$$

Here the k-th kernel $K_k$ is a d-dimensional matrix (in this embodiment a two-dimensional matrix), which is usually small compared to the number of nodes 512-518 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 512-520 in the respective layer 502-510. In particular, for a convolutional layer 504, the number of nodes 514 in the convolutional layer is equivalent to the number of nodes 512 in the preceding layer 502 multiplied with the number of kernels.

If the nodes 512 of the preceding layer 502 are arranged as a d-dimensional matrix, using a plurality of kernels can be interpreted as adding a further dimension (denoted as "depth" dimension), so that the nodes 514 of the convolutional layer 504 are arranged as a (d+1)-dimensional matrix. If the nodes 512 of the preceding layer 502 are already arranged as a (d+1)-dimensional matrix comprising a depth dimension, using a plurality of kernels can be interpreted as expanding along the depth dimension, so that the nodes 514 of the convolutional layer 504 are arranged also as a (d+1)-dimensional matrix, wherein the size of the (d+1)-dimensional matrix with respect to the depth dimension is by a factor of the number of kernels larger than in the preceding layer 502.

The advantage of using convolutional layers 504 is that spatially local correlation of the input data can exploited by enforcing a local connectivity pattern between nodes of adjacent layers, in particular by each node being connected to only a small region of the nodes of the preceding layer.

In embodiment shown in FIG. 5, the input layer 502 comprises 36 nodes 512, arranged as a two-dimensional 6×6 matrix. The convolutional layer 504 comprises 72 nodes 514, arranged as two two-dimensional 6×6 matrices, each of the two matrices being the result of a convolution of the values of the input layer with a kernel. Equivalently, the nodes 514 of the convolutional layer 504 can be interpreted as arranges as a three-dimensional 6×6×2 matrix, wherein the last dimension is the depth dimension.

A pooling layer 506 can be characterized by the structure and the weights of the incoming edges and the activation function of its nodes 516 forming a pooling operation based on a non-linear pooling function f. For example, in the two dimensional case the values $x^{(n)}$ of the nodes 516 of the pooling layer 506 can be calculated based on the values $x^{(n-1)}$ of the nodes 514 of the preceding layer 504 as $$x^{(n)} = f\left(x^{(n-1)}[id_1, jd_2], \dots , x^{(n-1)}[id_1 + d_1 - 1, jd_2 + d_2 - 1]\right)$$

In other words, by using a pooling layer 506, the number of nodes 514, 516 can be reduced, by replacing a number $d1 \cdot d2$ of neighboring nodes 514 in the preceding layer 504 with a single node 516 being calculated as a function of the values of said number of neighboring nodes in the pooling layer. In particular, the pooling function f can be the max-function, the average or the L2-Norm. In particular, for a pooling layer 506 the weights of the incoming edges are fixed and are not modified by training.

The advantage of using a pooling layer 506 is that the number of nodes 514, 516 and the number of parameters is reduced. This leads to the amount of computation in the network being reduced and to a control of overfitting.

In the embodiment shown in FIG. 5, the pooling layer 506 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 508 can be characterized by the fact that a majority, in particular, all edges between nodes 516 of the previous layer 506 and the nodes 518 of the fully-connected layer 508 are present, and wherein the weight of each of the edges can be adjusted individually.

In this embodiment, the nodes 516 of the preceding layer 506 of the fully-connected layer 508 are displayed both as two-dimensional matrices, and additionally as non-related nodes (indicated as a line of nodes, wherein the number of nodes was reduced for a better presentability). In this embodiment, the number of nodes 518 in the fully connected layer 508 is equal to the number of nodes 516 in the preceding layer 506. Alternatively, the number of nodes 516, 518 can differ.

Furthermore, in this embodiment, the values of the nodes 520 of the output layer 510 are determined by applying the Softmax function onto the values of the nodes 518 of the preceding layer 508. By applying the Softmax function, the sum the values of all nodes 520 of the output layer 510 is 1, and all values of all nodes 520 of the output layer are real numbers between 0 and 1.

A convolutional neural network 500 can also comprise a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/dense neural networks), element-wise multiplication (attention) or other differentiable operators. Therefore, the convolutional neural network architecture can be nested rather than being sequential if the whole pipeline is differentiable.

In particular, convolutional neural networks 500 can be trained based on the backpropagation algorithm. For preventing overfitting, methods of regularization can be used, e.g. dropout of nodes 512-520, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another datasets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 1-3. Certain steps or functions of the methods and workflows described herein, including one or more of the steps or functions of FIGS. 1-3, may be performed by a server or by another processor in a network-based cloud-computing system. Certain steps or functions of the methods and workflows described herein, including one or more of the steps of FIGS. 1-3, may be performed by a client computer in a network-based cloud computing system. The steps or functions of the methods and workflows described herein, including one or more of the steps of FIGS. 1-3, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 1-3, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 6:
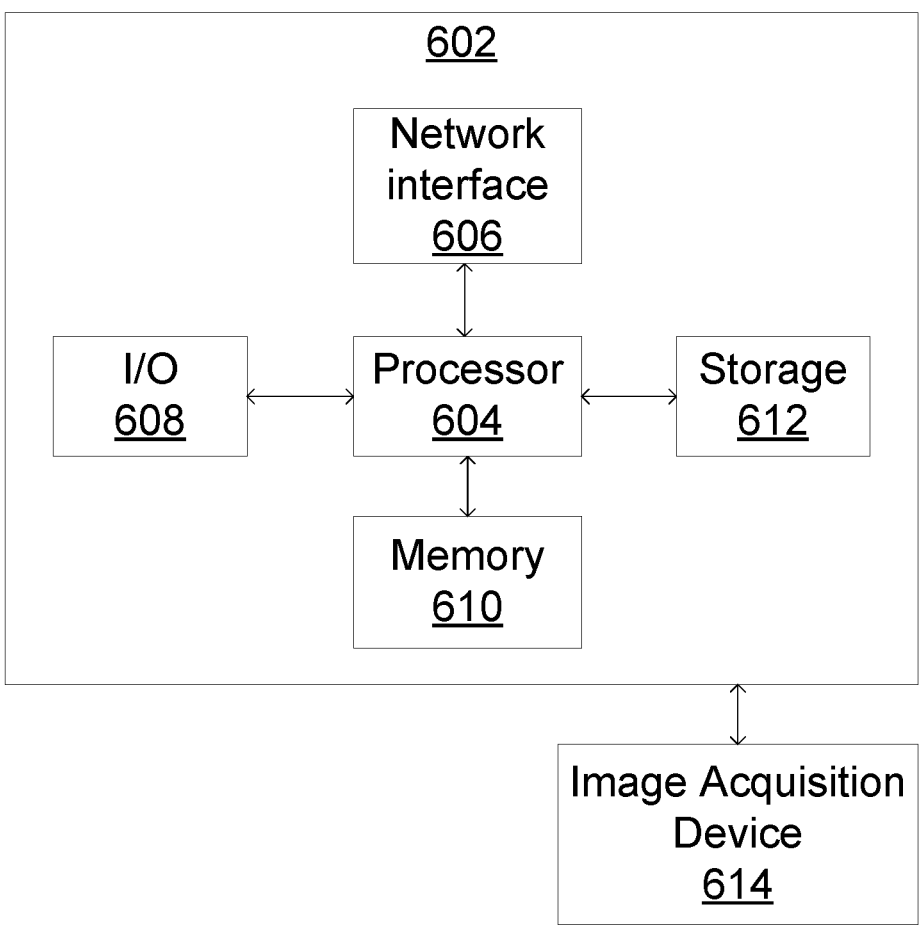
FIG. 6 shows a high-level block diagram of a computer that may be used to implement one or more embodiments.

A high-level block diagram of an example computer 602 that may be used to implement systems, apparatus, and methods described herein is depicted in FIG. 6. Computer 602 includes a processor 604 operatively coupled to a data storage device 612 and a memory 610. Processor 604 controls the overall operation of computer 602 by executing computer program instructions that define such operations. The computer program instructions may be stored in data storage device 612, or other computer readable medium, and loaded into memory 610 when execution of the computer program instructions is desired. Thus, the method and workflow steps or functions of FIGS. 1-3 can be defined by the computer program instructions stored in memory 610 and/or data storage device 612 and controlled by processor 604 executing the computer program instructions. For example, the computer program instructions can be implemented as computer executable code programmed by one skilled in the art to perform the method and workflow steps or functions of FIGS. 1-3. Accordingly, by executing the computer program instructions, the processor 604 executes the method and workflow steps or functions of FIGS. 1-3. Computer 602 may also include one or more network interfaces 606 for communicating with other devices via a network. Computer 602 may also include one or more input/output devices 608 that enable user interaction with computer 602 (e.g., display, keyboard, mouse, speakers, buttons, etc.).

Processor 604 may include both general and special purpose microprocessors, and may be the sole processor or one of multiple processors of computer 602. Processor 604 may include one or more central processing units (CPUs), for example. Processor 604, data storage device 612, and/or memory 610 may include, be supplemented by, or incorporated in, one or more application-specific integrated circuits (ASICs) and/or one or more field programmable gate arrays (FPGAs).

Data storage device 612 and memory 610 each include a tangible non-transitory computer readable storage medium. Data storage device 612, and memory 610, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 608 may include peripherals, such as a printer, scanner, display screen, etc. For example, input/output devices 608 may include a display device such as a cathode ray tube (CRT) or liquid crystal display (LCD) monitor for displaying information to the user, a keyboard, and a pointing device such as a mouse or a trackball by which the user can provide input to computer 602.

An image acquisition device 614 can be connected to the computer 602 to input image data (e.g., medical images) to the computer 602. It is possible to implement the image acquisition device 614 and the computer 602 as one device. It is also possible that the image acquisition device 614 and the computer 602 communicate wirelessly through a network. In a possible embodiment, the computer 602 can be located remotely with respect to the image acquisition device 614.

Any or all of the systems and apparatus discussed herein may be implemented using one or more computers such as computer 602.

One skilled in the art will recognize that an implementation of an actual computer or computer system may have other structures and may contain other components as well, and that FIG. 6 is a high level representation of some of the components of such a computer for illustrative purposes.

Independent of the grammatical term usage, individuals with male, female or other gender identities are included within the term.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The following is a list of non-limiting illustrative embodiments disclosed herein:

Illustrative embodiment 1. A computer-implemented method comprising: receiving one or more input medical images; selecting one or more modality-specific expert subnetworks of a machine learning based model for performing a first processing of the one or more input medical images; performing the first processing of the one or more input medical images for performing a medical imaging analysis task using the one or more selected modality-specific expert subnetworks; merging results of the first processing into one or more sets of merged results; selecting one or more cross-modality expert subnetworks of the machine learning based model for performing a second processing of the one or more sets of merged results; performing the second processing of the one or more sets of merged results for performing the medical imaging analysis task using the one or more selected cross-modality expert subnetworks; and outputting results of the second processing.

Illustrative embodiment 2. The computer-implemented method of illustrative embodiment 1, wherein the machine learning based model is trained via self-supervised learning.

Illustrative embodiment 3. The computer-implemented method of any one of illustrative embodiments 1-2, wherein performing the first processing of the one or more input medical images for performing a medical imaging analysis task using the one or more selected modality-specific expert subnetworks comprises: processing modality-specific data of the one or more input medical images using the one or more selected modality-specific expert subnetworks.

Illustrative embodiment 4. The computer-implemented method of any one of illustrative embodiments 1-3, wherein performing the second processing of the one or more sets of merged results for performing the medical imaging analysis task using the one or more selected cross-modality expert subnetworks comprises: integrating the one or more sets of merged results between each other.

Illustrative embodiment 5. The computer-implemented method of any one of illustrative embodiments 1-4, wherein a number of modality-specific expert subnetworks in the machine learning based network is learned for each modality during a training of the machine learning based network.

Illustrative embodiment 6. The computer-implemented method of any one of illustrative embodiments 1-5, wherein a number of modality-specific expert subnetworks in the machine learning based network is predefined for each modality.

Illustrative embodiment 7. The computer-implemented method of any one of illustrative embodiments 1-6, wherein a number of cross-modality expert subnetworks in the machine learning based network is learned during training of the machine learning based network.

Illustrative embodiment 8. The computer-implemented method of any one of illustrative embodiments 1-7, wherein a number of layers and a number of parameters of each of the layer for each modality-specific expert subnetwork and each cross-modality expert subnetworks in the machine learning based network are defined based on resource availability.

Illustrative embodiment 9. The computer-implemented method of any one of illustrative embodiments 1-8, wherein the machine learning based model is a foundational model.

Illustrative embodiment 10. An apparatus comprising: means for receiving one or more input medical images; means for selecting one or more modality-specific expert subnetworks of a machine learning based model for performing a first processing of the one or more input medical images; means for performing the first processing of the one or more input medical images for performing a medical imaging analysis task using the one or more selected modality-specific expert subnetworks; means for merging results of the first processing into one or more sets of merged results; means for selecting one or more cross-modality expert subnetworks of the machine learning based model for performing a second processing of the one or more sets of merged results; means for performing the second processing of the one or more sets of merged results for performing the medical imaging analysis task using the one or more selected cross-modality expert subnetworks; and means for outputting results of the second processing.

Illustrative embodiment 11. The apparatus of illustrative embodiment 10, wherein the machine learning based model is trained via self-supervised learning.

Illustrative embodiment 12. The apparatus of any one of illustrative embodiments 10-11, wherein the means for performing the first processing of the one or more input medical images for performing a medical imaging analysis task using the one or more selected modality-specific expert subnetworks comprises: means for processing modality-specific data of the one or more input medical images using the one or more selected modality-specific expert subnetworks.

Illustrative embodiment 13. The apparatus of any one of illustrative embodiments 10-12, wherein the means for performing the second processing of the one or more sets of merged results for performing the medical imaging analysis task using the one or more selected cross-modality expert subnetworks comprises: means for integrating the one or more sets of merged results between each other.

Illustrative embodiment 14. The apparatus of any one of illustrative embodiments 10-13, wherein a number of modality-specific expert subnetworks in the machine learning based network is learned for each modality during training of the machine learning based network.

Illustrative embodiment 15. A non-transitory computer readable medium storing computer program instructions, the computer program instructions when executed by a processor cause the processor to perform operations comprising: receiving one or more input medical images; selecting one or more modality-specific expert subnetworks of a machine learning based model for performing a first processing of the one or more input medical images; performing the first processing of the one or more input medical images for performing a medical imaging analysis task using the one or more selected modality-specific expert subnetworks; merging results of the first processing into one or more sets of merged results; selecting one or more cross-modality expert subnetworks of the machine learning based model for performing a second processing of the one or more sets of merged results; performing the second processing of the one or more sets of merged results for performing the medical imaging analysis task using the one or more selected cross-modality expert subnetworks; and outputting results of the second processing.

Illustrative embodiment 16. The non-transitory computer readable medium of illustrative embodiment 15, wherein the machine learning based model is trained via self-supervised learning.

Illustrative embodiment 17. The non-transitory computer readable medium of any one of illustrative embodiments 15-16, wherein a number of modality-specific expert subnetworks in the machine learning based network is predefined for each modality.

Illustrative embodiment 18. The non-transitory computer readable medium of any one of illustrative embodiments 15-17, wherein a number of cross-modality expert subnetworks in the machine learning based network is learned during training of the machine learning based network.

Illustrative embodiment 19. The non-transitory computer readable medium of any one of illustrative embodiments 15-18, wherein a number of layers and a number of parameters of each of the layer for each modality-specific expert subnetwork and each cross-modality expert subnetworks in the machine learning based network are defined based on resource availability.

Illustrative embodiment 20. The non-transitory computer readable medium of any one of illustrative embodiments 15-19, wherein the machine learning based model is a foundational model.

The invention claimed is:

1. A computer-implemented method comprising:
receiving one or more input medical images;
selecting one or more modality-specific expert subnetworks of a machine learning based model for performing a first processing of the one or more input medical images;
performing the first processing of the one or more input medical images for performing a medical imaging analysis task using the one or more selected modality-specific expert subnetworks;
merging results of the first processing into one or more sets of merged results;

selecting one or more cross-modality expert subnetworks of the machine learning based model for performing a second processing of the one or more sets of merged results;
performing the second processing of the one or more sets of merged results for performing the medical imaging analysis task using the one or more selected cross-modality expert subnetworks; and
outputting results of the second processing.

2. The computer-implemented method of claim 1, wherein the machine learning based model is trained via self-supervised learning.

3. The computer-implemented method of claim 1, wherein performing the first processing of the one or more input medical images for performing a medical imaging analysis task using the one or more selected modality-specific expert subnetworks comprises:
processing modality-specific data of the one or more input medical images using the one or more selected modality-specific expert subnetworks.

4. The computer-implemented method of claim 1, wherein performing the second processing of the one or more sets of merged results for performing the medical imaging analysis task using the one or more selected cross-modality expert subnetworks comprises:
integrating the one or more sets of merged results between each other.

5. The computer-implemented method of claim 1, wherein a number of modality-specific expert subnetworks in the machine learning based network is learned for each modality during training of the machine learning based network.

6. The computer-implemented method of claim 1, wherein a number of modality-specific expert subnetworks in the machine learning based network is predefined for each modality.

7. The computer-implemented method of claim 1, wherein a number of cross-modality expert subnetworks in the machine learning based network is learned during training of the machine learning based network.

8. The computer-implemented method of claim 1, wherein a number of layers and a number of parameters of each of the layer for each modality-specific expert subnetwork and each cross-modality expert subnetworks in the machine learning based network are defined based on resource availability.

9. The computer-implemented method of claim 1, wherein the machine learning based model is a foundational model.

10. An apparatus comprising:
means for receiving one or more input medical images;
means for selecting one or more modality-specific expert subnetworks of a machine learning based model for performing a first processing of the one or more input medical images;
means for performing the first processing of the one or more input medical images for performing a medical imaging analysis task using the one or more selected modality-specific expert subnetworks;
means for merging results of the first processing into one or more sets of merged results;
means for selecting one or more cross-modality expert subnetworks of the machine learning based model for performing a second processing of the one or more sets of merged results;
means for performing the second processing of the one or more sets of merged results for performing the medical imaging analysis task using the one or more selected cross-modality expert subnetworks; and means for outputting results of the second processing.

11. The apparatus of claim 10, wherein the machine learning based model is trained via self-supervised learning.

12. The apparatus of claim 10, wherein the means for performing the first processing of the one or more input medical images for performing a medical imaging analysis task using the one or more selected modality-specific expert subnetworks comprises:

means for processing modality-specific data of the one or more input medical images using the one or more selected modality-specific expert subnetworks.

13. The apparatus of claim 10, wherein the means for performing the second processing of the one or more sets of merged results for performing the medical imaging analysis task using the one or more selected cross-modality expert subnetworks comprises:

means for integrating the one or more sets of merged results between each other.

14. The apparatus of claim 10, wherein a number of modality-specific expert subnetworks in the machine learning based network is learned for each modality during training of the machine learning based network.

15. A non-transitory computer readable medium storing computer program instructions, the computer program instructions when executed by a processor cause the processor to perform operations comprising:

receiving one or more input medical images;

selecting one or more modality-specific expert subnetworks of a machine learning based model for performing a first processing of the one or more input medical images;

performing the first processing of the one or more input medical images for performing a medical imaging analysis task using the one or more selected modality-specific expert subnetworks;

merging results of the first processing into one or more sets of merged results;

selecting one or more cross-modality expert subnetworks of the machine learning based model for performing a second processing of the one or more sets of merged results;

performing the second processing of the one or more sets of merged results for performing the medical imaging analysis task using the one or more selected cross-modality expert subnetworks; and outputting results of the second processing.

16. The non-transitory computer readable medium of claim 15, wherein the machine learning based model is trained via self-supervised learning.

17. The non-transitory computer readable medium of claim 15, wherein a number of modality-specific expert subnetworks in the machine learning based network is predefined for each modality.

18. The non-transitory computer readable medium of claim 15, wherein a number of cross-modality expert subnetworks in the machine learning based network is learned during training of the machine learning based network.

19. The non-transitory computer readable medium of claim 15, wherein a number of layers and a number of parameters of each of the layer for each modality-specific expert subnetwork and each cross-modality expert subnetworks in the machine learning based network are defined based on resource availability.

20. The non-transitory computer readable medium of claim 15, wherein the machine learning based model is a foundational model.

* * * * *